United States Patent [19]

Termin

[11] Patent Number: 5,514,594
[45] Date of Patent: May 7, 1996

[54] METHOD FOR MEASUREMENT OF NO CONTENTS

[76] Inventor: Andreas P. Termin, 400 Raymondale Dr. #11, South Pasadena, Calif. 91030

[21] Appl. No.: 262,627

[22] Filed: Jun. 20, 1994

Related U.S. Application Data

[62] Division of Ser. No. 144,198, Oct. 27, 1993, Pat. No. 5,374,397.

[30] Foreign Application Priority Data

Nov. 2, 1992 [DE] Germany ............................ 42 36 944.4

[51] Int. Cl.$^6$ .................................................. G01N 33/00
[52] U.S. Cl. ............................................. 436/116; 436/117
[58] Field of Search ..................................... 436/107, 109, 436/116, 117, 172

[56] References Cited

FOREIGN PATENT DOCUMENTS

| | | |
|---|---|---|
| 249912A2 | 6/1987 | European Pat. Off. |
| 2225696A1 | 12/1972 | Germany. |

OTHER PUBLICATIONS

Peter Mordvintcev, et al., "On Line Detection of Nitric Oxide Formation in Liquid Aqueous Phase by Electron Paramagnetic Resonance Spectroscopy," Analytical Biochemistry 199, 142 146 (1991).

Mark Bollinger and Robert E. Sievers, "Conversion of Nitrogen Dioxide, Nitric Acid, and n–Propyl Nitrate to Nitric Oxide by Gold–Catalyzed Reduction with Carbon Monoxide" Anal. Chem. 1983, 55, 1980–1986.

Oliver C. Zafiriou and Mack McFarland, "Determination of Trace Levels of Nitric Oxide in Aqueous Solution", Anal. Chem. 1980, 52, 1662–1667.

Chemical Abstracts, vol. 113, (16), 1990, Ref.: 139557g.

*Primary Examiner*—David A. Redding
*Attorney, Agent, or Firm*—Blakely, Sokoloff, Taylor & Zafman

[57] ABSTRACT

The present invention relates to a method and a device for the measurement of NO contents in liquids using an inert carder gas. The device consists of a micro reaction part FIG. 1 which is divided into an inert gas inlet nozzle 1, the microreaction vessel 2 with frit 3, at least one inlet nozzle for the injection of the liquid to be analyzed 4, as well as a cooled outlet nozzle for the inert gas loaded with NO 5, and a detector 6, with which the NO content of the inset liquid is measured and evaluated, and where the $NO_2-$ ions present in the solution are reduced back to NO using a reaction mixture consisting out of 1,1'-dimethylferrocene in acetonitrile in an acidic medium, preferably perchloric acid.

8 Claims, 2 Drawing Sheets

METHOD FOR MEASUREMENT OF NO CONTENTS

This application is a divisional of U.S. patent application Ser. No. 08/144,198, filed Oct. 27, 1993, now U.S. Pat. No. 5,374,397.

BACKGROUND OF THE INVENTION

1. Field of the Invention

Nitric oxide is a short lived radical and has recently been found to be produced by various mammalian cells e.g. endothelial cells, macrophages and nerve cells. It influences the blood pressure, is a neurotransmitter and a tool of the immune response.

The detection and evaluation of the nitric oxide (NO) can be performed in different ways.

2. Related Art

The state of art shows different methods for detecting nitric oxide, for example as a color complex using sulfanile acid (1) (diazotation with NO and coupling with N (1-naphtyldiamine)), or with oxyhemoglobin (2), ESR-spectroscopic (3), mass-spectroscopic (4), with the help of spin-traps (5), electrochemical (6) or using chemiluminescence (7).

The chemiluminescence method used in the present inventive method relates to the reaction of NO and ozone to $NO_2^*$ and $O_2$. During the subsequent decay of $NO_2^*$ light of the wavelength 600–875 nm is emitted, which can be measured using a photodetector.

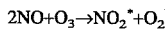

Nitric oxide is a very reactive gas, that can be easily oxidized to $NO_2-$ (nitrite) in the presence of oxygen. For evaluating the exact amount of NO in liquids it is necessary to reduce the nitrite formed as an intermediate back to NO.

According to the current state of the art (8) a reaction vessel with refluxing acidic acid containing 1% sodium iodide (NaI) is used and NO/water solutions are used as standards.

The sample is introduced into the reducing medium which is purged with helium for approximately 60 sec. A valve to the NO-detector is opened and the NO is transferred into the NO detector. An alkaline cooling trap prevents that the acidic vapors contaminate the NO-detector. This system displays the following disadvantages:

a) the reaction vessel has to be heated, b) the temperature of the reaction vessel has to be hold precisely to prevent fluctuations of the ground signal, c) the hot acidic acid vapors have to be cooled down and afterwards the gas stream has to be fed through an alkaline cooling trap, which leads to a considerable expansion of the total volume of the device followed by a reduction of the NO concentration in the gas stream, and therefore to measurement inaccuracies.

d) work intensive standard curves have to be done e) the reduction is considerably slow {~1 minute}(9)

SUMMARY OF THE INVENTION

The task of the present invention was to find particularly mild reducing conditions, which is important for analyzing physiological liquids, like for example effluents from cell preparations. Physiological liquids contain various organic compounds that will be also reduced, if the conditions are too harsh. Furthermore, there are limitations to overcome due to the limited amount of reduction medium in a micro reaction vessel.

Therefore, the inventive task was to eliminate all of the above described insufficiencies by simplifying the procedure. It should be carried out at room temperature leading to a reduction in measurement fluctuations, and to achieve a high sensibility of the method by reducing the total volume of the device. Furthermore, continuous sampling should be possible.

This task was resolved by a method for the reduction of $NO_2-$ to nitric oxide in liquids containing nitric oxide, wherein said, that the reaction runs in the apparatus according to FIG. 1 using an inert carrier gas. The micro reaction part FIG. 1 is subdivided into the inert gas inlet nozzle 1, the micro reaction vessel 2 with frit 3, at least one inlet nozzle for the liquid to be analyzed 4, a cooled outlet nozzle for the inert gas loaded with NO 5, and a detector for measuring and evaluating the NO-content of the liquid. The reaction can be carded out at a temperature range of 5° C.–50° C. The reaction medium consists of 1,1'dimethylferrocene in acetonitrile under acidic conditions. The mixing of the reaction medium is achieved by an inert gas stream that is fed into the reaction medium through a frit and the inert gas is used simultaneously as carrier gas for the nitric oxide, which is carded via outlet nozzle 5 to the detector 6 where the total NO content is analyzed. Preferably, 70% perchloric acid is used as acidic medium and room temperature is the chosen reaction temperature. The reduction is exothermic and extremely fast (10).

Due to the low reaction temperature and the relatively high boiling point of the reaction media and to the very low flow of the inert carrier gas through the reaction medium, the rise in vapor partial pressure is that small that it can be neglected. These circumstances proved to be an advantage for the total concept, method and device, because undesired brine particles do not reach the detection part of the apparatus FIG. 2. Furthermore, cooling devices that increase the total volume are not necessary. Therefore, the outlet nozzle 5 is only designed as a pipe surrounded by a cooling mantle 7, cooled by constant water flow (~10° C.). Inert gases used are noble gases, preferably helium.

A further advantageous development of the new method for analyzing physiological effluents of cell preparations is that the liquid to be analyzed for its NO content is directly injected into the reaction medium in vessel 2 via inlet nozzle 4 through the septum 8 in FIG. 1. This reduces measurement fluctuations due to possible spilling of the liquid sample at the glass parts of the device. A stable sodium nitrite solution is used as standard control. The 1,1'dimethylferrocene/acetonitrile/perchloric acid mixture with a perchloric acid concentration of preferably 1% used in the new inventive method also displays the advantage that it can be hardly affected by dilution. Therefore, continuous sampling into the same reducing solution is possible. FIG. 3 shows measurements in which 500 pmol sodium nitrite diluted in 100 µl water am added each time to the 2,15 ml reduction medium. The signal displayed in mV stays almost the same.

DESCRIPTION OF THE DRAWINGS

The following descriptions and examples describe the invention in detail.

The micro reaction part FIG. 1 is subdivided into the inert gas inlet nozzle 1, the micro reaction vessel 2 with frit 3, at least one inlet nozzle for the liquid to be analyzed 4, an outlet nozzle for the inert gas loaded with NO 5 surrounded by a cooling mantle 7. The samples are injected through the septum 8. The gas flow or the evacuation of the micro reaction vessel are controlled by vacuum tight Teflon valves 16, 17. Total volume of the apparatus from the frit 3 to the teflon stopcock 17 is 35 ml; inner diameter of the inlet and outlet nozzle is 4 mm; inner diameter of the microreaction vessel 2 is 20 mm.

Figure 1:
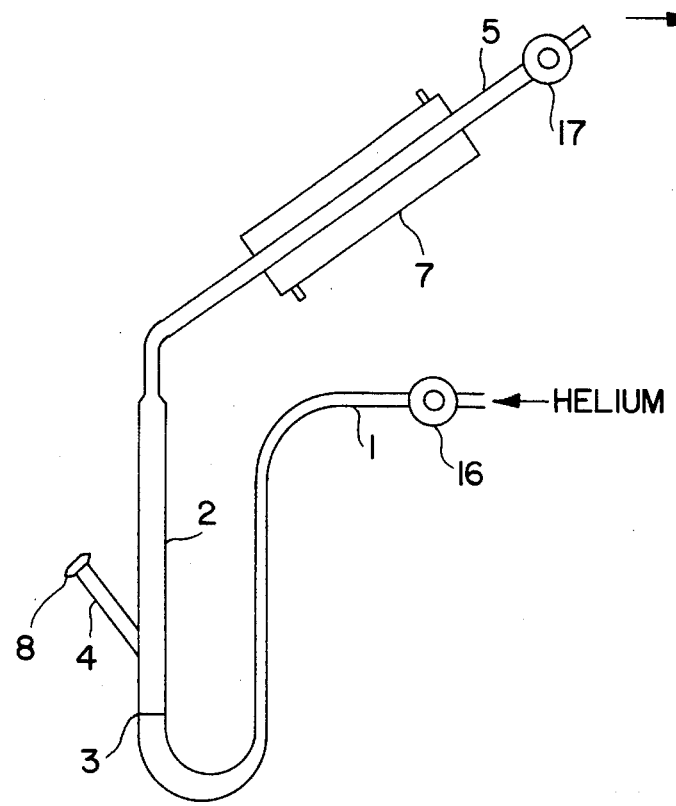
FIG.1 shows a device for the reduction of $NO/NO_2-$—containing solutions. The total NO content is set free and carried to the detector and recorder unit FIG. 2, where the total NO content is evaluated.
Figure 2:
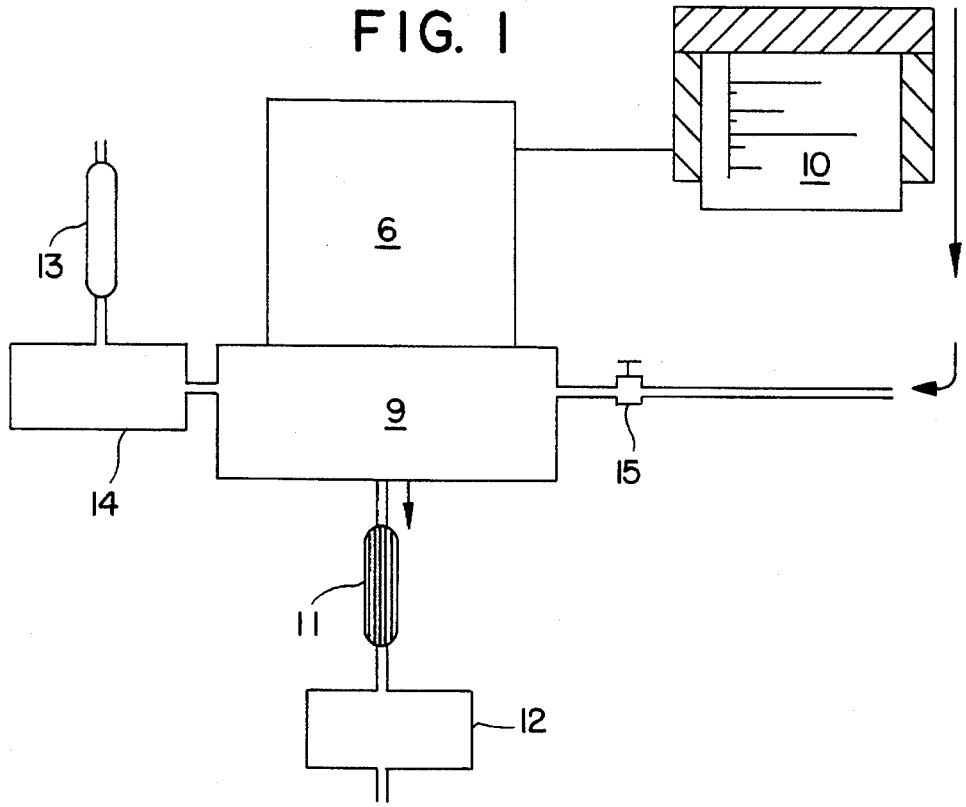
FIG. 2. shows the NO detector and recorder.
Figure 3:
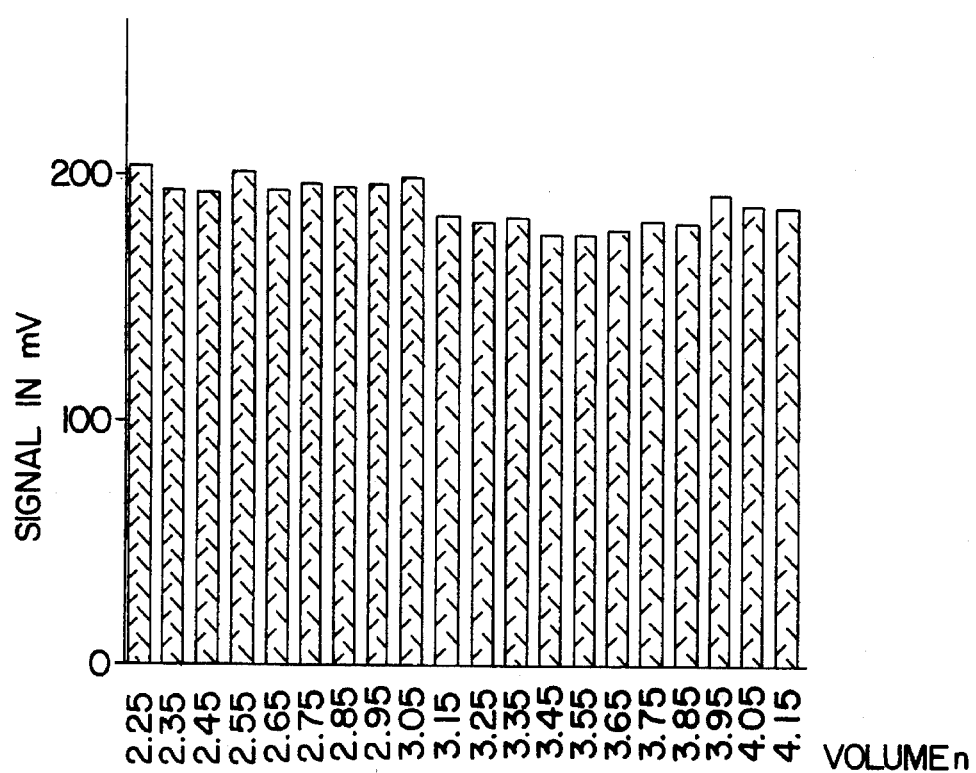
FIG. 3. 500 μmol sodium nitrite diluted in 100 μl water is added each time to 2.15 ml of the reducing solution; the signal indicated by mV is almost not affected by the dilution.

After leaving the microreaction part FIG. 1 the inert gas stream carries the nitric oxide to the NO-analyzer, where the NO-detector 6 measures the emitted light in the chemiluminescence generator 9 the data are recorded 10. The NO-analyzer is equipped with a active charcoal filter 11 (to destroy residues of ozone), a vacuum pump 12 to maintain a proper vacuum in the reaction chamber and an oxygen supply 13 for the ozone generator 14. The valve 15 regulates the flow of the carrier gas into the chemiluminescence generator 9.

PREFERRED EMBODIMENT

The inventive method and device is used for the determination of NO release by mammalian cells. Bovine endothelial cells, for example, are detached from the inner wall of bovine aortas using collagenase and transferred to microcarrier beads. The cell density is defined and a cell aliquot (120 billion cells) are transferred onto a filter, 105 μm pore diameter and superfused with Krebs-Henseleit solution at a known rate with a temperature of 37° C. The filtrate is then injected into the device of FIG. 1 for the determination of its NO content. The NO determination is carded out under normal conditions. No preventive measures are taken with regard to the oxidation of the NO to $NO_2-$. In order to determine the total nitrogen oxide content the meanwhile formed $NO_2-$ has to be reduced to NO. For this purpose a reduction solution consisting of 30 mg 1,1'dimethylferrocene solved in 3 ml HPLC grade acetonitrile acidified by 49 μl of perchloric acid (70%) has been prepared. 2 ml of this solution is introduced via inlet nozzle 4 into the device of FIG. 1. In advance, the inlet valve 16 has been opened and helium has been infused into the apparatus with a flow of 35 ml per minute. Simultaneously the outlet valve 17 and the regulation valve 15 have been opened. 200 μl of the above described fresh cell effluents are now injected using a gastight syringe through the injection septum 8 via inlet nozzle 4 directly into the reduction solution of the microreaction vessel 2. The sample contains the NO content produced by 120 billion freshly harvested endothelial cells.

The cooling water in the cooling mantle 7 has a temperature of 10° C. NO leaves the vessel via outlet nozzle, 5 carded by a helium stream into the chemluminescence generator 9, where the emitted light displays a wavelength of 600–875 nm and is proportional to the NO concentration in the gas stream. The NO concentration is indicated as pmol/ml.

Five different experiments lead to the; following NO values expressed as pmol per analyzed filtrate.

| | |
|---|---|
| 1 | 232 pmol |
| 2 | 162 pmol |
| 3 | 874 pmol |
| 4 | 675 pmol |
| 5 | 426 pmol |

The following data of dimensions display the volume minimization of the device according to FIG. 1.

Figure 4:
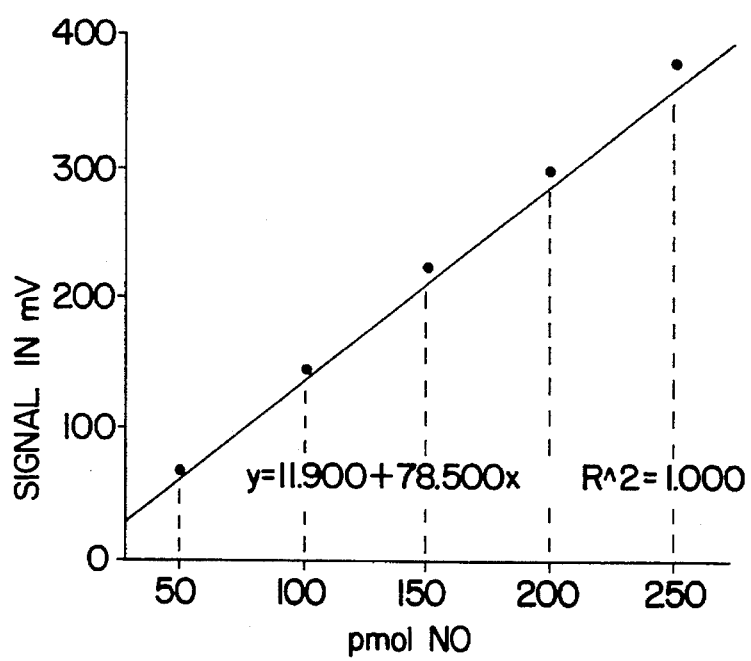
FIG. 4 is a standard curve produced by using the new method.

The NO standard curve is obtained by injecting small volumes of defined amounts of dissolved sodium nitrite, which is reduced to NO according to the inventive method, proved the high precision and reproducibility of the new method as displayed in FIG. 4.

I claim:

1. A method for reducing $NO_2-$ ions into nitric oxide in liquids containing nitric oxide, wherein said method is carried out at a temperature of 5° C.–50° C. and comprises the steps of:

providing a device including a micro reaction vessel with frit, an inlet nozzle with injection septum, an inert gas inlet nozzle attached to a first end of said reaction vessel, an outlet nozzle attached to a second end of said reaction vessel, means for cooling said outlet nozzle, and a detector;

introducing a reducing solution consisting of 1,1'-dimethylferrocene in acetonitrile in an acidic medium into the micro reaction vessel;

introducing a liquid containing nitric oxide into the reducing solution in the micro reaction vessel to form a reaction solution; and mixing the reaction solution by an inert gas stream which is infused into the reaction solution through the frit, where the inert gas simultaneously acts as a carrier gas for the nitric oxide gas, which is transported via the outlet nozzle to the detector where total nitric oxide content is determined.

2. The method of claim 1, wherein the reducing solution is made acidic by adding 70% perchloric acid and the method is carried out at room temperature.

3. The method of claim 1 and 2, wherein the reaction is fast enough to allow continuous sampling.

4. The method of claim 1 and 2, wherein the liquids containing nitric oxide are physiological fluids obtained as effluents from fresh mammalian cells.

5. The method of claims 1 to 3, wherein the liquids containing nitric oxide are directly injected into the reducing solution.

6. The method of claim 1, wherein the inert gas is infused through the inert gas inlet nozzle which is regulated by the inlet valve, further wherein the inert gas flows from the inert gas inlet nozzle to the micro reaction vessel through the frit.

7. The method of claim 1, wherein the reducing solution is introduced into the micro reaction vessel through the inlet nozzle.

8. The method of claim 1, wherein the liquid containing nitric oxide is injected, using a gastight syringe through the injection septum, via the inlet nozzle directly into the reducing solution in the micro reaction vessel.

* * * * *

UNITED STATES PATENT AND TRADEMARK OFFICE
CERTIFICATE OF CORRECTION

PATENT NO.  : 5, 514, 594
DATED       : May 7, 1996
INVENTOR(S) : Andreas P. Termin It is certified that errors appear in the above-identified patent and that said Letters Patent is hereby corrected as shown below:

Title page,
In the Abstract [57] at line 11, pleae delete " -dimethylferrocene " and insert -- dimethylferrocene --.

In column 2 at line 22, please delete " carded " and insert -- carried --.

In column 2 at line 28, please delete " carded " and insert -- carried --.

In column 2 at line 60, please delete " am " and insert -- are --.

In column 3 at line 42, please delete " carded " and insert -- carried --.

UNITED STATES PATENT AND TRADEMARK OFFICE
CERTIFICATE OF CORRECTION

PATENT NO. : 5,514,594
DATED : May 7, 1996
INVENTOR(S) : Andreas P. Termin

It is certified that errors appear in the above-identified patent and that said Letters Patent is hereby corrected as shown below:

In column 3 at line 61, please delete " nozzle, " and insert -- nozzle --.

In column 3 at line 62, please delete " carded " and insert -- carried --.

In column 3 at line 62, please delete " chemluminescence " and insert -- chemiluminescence --.

In column 4 at line 30, please delete "-dimethylferrocene " and insert -- dimethylferrocene --.

Signed and Sealed this

Twenty-fourth Day of September, 1996

Attest:

BRUCE LEHMAN

Attesting Officer     Commissioner of Patents and Trademarks